(12) United States Patent
Kotani

(10) Patent No.: US 7,986,769 B2
(45) Date of Patent: Jul. 26, 2011

(54) RADIOGRAPHIC IMAGE DETECTION APPARATUS AND METHOD FOR CONTROLLING THE APPARATUS

(75) Inventor: Manabu Kotani, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 100 days.

(21) Appl. No.: 12/588,347

(22) Filed: Oct. 13, 2009

(65) Prior Publication Data

US 2010/0091945 A1    Apr. 15, 2010

(30) Foreign Application Priority Data

Oct. 15, 2008 (JP) ................................. 2008-265866

(51) Int. Cl.
*H05G 1/10* (2006.01)

(52) U.S. Cl. .......................................... 378/95; 378/62

(58) Field of Classification Search .................... 378/62, 378/95, 98.8, 108
See application file for complete search history.

(56) References Cited

FOREIGN PATENT DOCUMENTS

| JP | 11-126890   | 5/1999  |
|----|-------------|---------|
| JP | 2000-134539 | 5/2000  |
| JP | 2003-156565 | 5/2003  |
| JP | 2005-324015 | 11/2005 |

*Primary Examiner* — Courtney Thomas
(74) *Attorney, Agent, or Firm* — Jean C. Edwards, Esq.; Edwards Neils PLLC

(57) ABSTRACT

A region of interest is set in a state in which a subject is positioned in front of a radiographic image detector. Further, judgment is made as to whether a defect region is present in the region of interest. If the defect region is present in the region of interest, a relative movement amount of at least one of the subject and the radiographic image detector is calculated. After the at least one of the subject and the radiographic image detector is moved by the calculated relative movement amount, radiography is performed to detect a radiographic image.

8 Claims, 5 Drawing Sheets

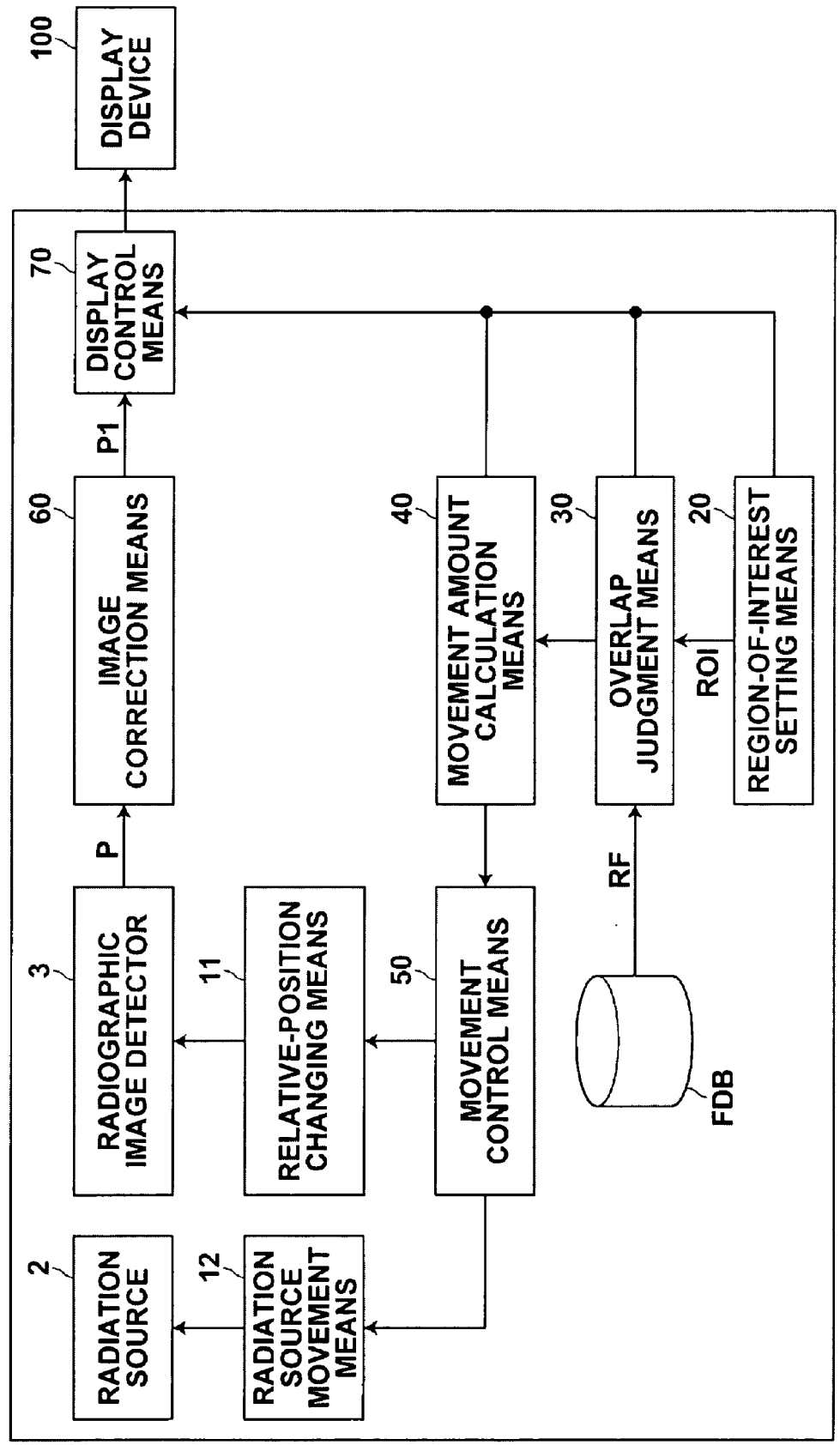

RADIOGRAPHIC IMAGE DETECTION APPARATUS AND METHOD FOR CONTROLLING THE APPARATUS

CROSS-REFERENCE TO RELATED APPLICATIONS

The present application claims priority from Japanese Patent Application No. 2008-265866, filed Oct. 15, 2008, the contents of which are herein incorporated by reference in their entirety.

BACKGROUND OF THE INVENTION

1. Field of the Invention

The present invention relates to a radiographic image detection apparatus that detects a radiographic image by irradiating a subject with radiation. Further, the present invention relates to a method for controlling the radiographic image detection apparatus.

2. Description of the Related Art

Conventionally, various kinds of radiation detectors (radiographic image detectors) have been proposed and practically used in medical fields, and the like. The radiation detectors store radiographic images related to subjects by irradiation with radiation that has passed through the subjects. One of the examples of such radiation detectors is a radiation detector using amorphous selenium, which generates charges by irradiation with radiation. Further, a so-called TFT-readout-type radiation detector, which uses an active matrix substrate, has been proposed. The active matrix substrate includes a plurality of divided electrodes, a plurality of storage capacitances (capacities) that store charges collected by each of the divided electrodes, and a plurality of TFT switches for reading out the charges stored in each of the storage capacitances.

In the radiographic image detectors, defect pixels are generated at some pixels, or dirt, dust or the like adheres to a top plate or the cover of the detector in some cases. In such cases, a defect region in which correct image information is not obtained is present in the radiographic image detector, and the presence of the defect region deteriorates the image quality of the radiographic image. Therefore, various methods have been proposed to prevent deterioration of the image quality caused by the defect region.

For example, Japanese Unexamined Patent Publication No. 11(1999)-126890 (Patent document 1) discloses a structure in which a radiographic image detector is replaceable for each predetermined unit element holder. In the radiographic image detector, when a defect is generated in a unit element holder, the unit element holder is replaced or repaired. Further, Japanese Unexamined Patent Publication No. 2005-324015 (Patent document 2) discloses a method for interpolating image data of a defect pixel based on image data of other pixels adjacent to the defect pixel.

Further, besides the techniques disclosed in Patent documents 1 and 2, a method for preventing deterioration of the image quality caused by the defect by moving the radiographic image detector has been proposed (please refer to Japanese Unexamined Patent Publication No. 2000-134539 (Patent document 3) and Japanese Unexamined Patent Publication No. 2003-156565 (Patent document 4) for example). Patent documents 3 and 4 propose radiography of a subject (a radiography target) by using normal pixels, other than the defect pixel, by moving the radiographic image detector relative to the subject.

However, in Patent documents 3 and 4, it is necessary to move the radiographic image detector to different positions and to perform radiography a plurality of times at the different positions to obtain a single radiographic image. Therefore, there is a problem that the dose of radiation that irradiates the subject becomes high.

SUMMARY OF THE INVENTION

In view of the foregoing circumstances, it is an object of the present invention to provide a radiographic image detection apparatus that can prevent deterioration of the image quality of a radiographic image caused by a defect region, while the dose of radiation that irradiates a subject is reduced. Further, it is another object of the present invention to provide a method for controlling the radiographic image detection apparatus.

A radiographic image detection apparatus of the present invention is a radiographic image detection apparatus comprising:

a radiation source that outputs radiation to a subject;

a radiographic image detector that obtains a radiographic image by detecting the radiation that has been output from the radiation source to the subject and that has passed through the subject;

a relative-position changing means that moves at least one of the radiographic image detector and the subject to change the relative positions of the radiographic image detector and the subject with respect to each other;

a defect-region storage means that stores the position of a defect region of the radiographic image detector;

a region-of-interest setting means that sets a region of interest in the radiographic image detector;

an overlap judgment means that judges whether the defect region stored in the defect-region storage means is included in the region of interest that has been set by the region-of-interest setting means;

a movement amount calculation means that calculates a relative movement amount for changing the relative positions so that the defect region is not included in the region of interest when the overlap judgment means has judged that the defect region is included in the region of interest; and a movement control means that controls, based on the relative movement amount that has been calculated by the movement amount calculation means, an operation of the relative-position changing means for moving the at least one of the radiographic image detector and the subject.

A method for controlling a radiographic image detection apparatus of the present invention is a method for controlling a radiographic image detection apparatus that includes:

a radiation source that outputs radiation to a subject;

a radiographic image detector that obtains a radiographic image by detecting the radiation that has been output from the radiation source to the subject and that has passed through the subject;

a relative-position changing means that moves at least one of the radiographic image detector and the subject to change the relative positions of the radiographic image detector and the subject with respect to each other; and a defect-region storage means, the method comprising the steps of:

setting a region of interest in the radiographic image detector;

judging whether a defect region that has been stored in the defect-region storage means in advance is included in the set region of interest;

calculating a relative movement amount for changing the relative positions so that the defect region is not included in the region of interest when it has been judged that the defect region is included in the region of interest; and moving, based on the calculated relative movement amount, the at least one of the radiographic image detector and the subject relative to each other by the relative-position changing means.

Here, the type of the radiographic image detector is not limited as long as the radiographic image detector detects, as a radiographic image, radiation that has passed through a subject. For example, the radiographic image detector may be a so-called TFT (thin-film transistor) type radiographic image detector. Alternatively, the radiographic image detector may be a so-called light-readout-type radiographic image detector.

The term "defect region" means a region in which correct readout of the image of the subject is impossible. For example, the defect region is generated when a defect pixel or pixels are present. However, the defect region is not limited to such a region. The defect region is generated also when dirt, dust or the like adheres to a cover of the detector or a top plate.

Further, the relative-position changing means may be a subject moving means, such as movable bed, which moves the subject with respect to the radiographic image detector. Alternatively, the relative-position changing means may be a detector moving means, which moves the radiographic image detector with respect to the subject. Further, the relative-position changing means may include both of the subject moving means and the detector moving means. The direction of moving the subject and/or the detector is not limited as long as the relative-position changing means changes the relative positions of the subject and the radiographic image detector with respect to each other. For example, the relative-position changing means may move the radiographic image detector and/or the subject in parallel to a detection surface of the radiographic image detector. Alternatively, the relative-position changing means may move the radiographic image detector and/or the subject rotationally with respect to the detection surface of the radiographic image detector.

Further, the defect-region storage means may store the size of the defect region (defect) and the degree of the defect of the defect region together with the position of the defect region. At this time, the overlap judgment means may judge whether the defect region having a size that is larger than or equal to a predetermined threshold value and the degree of the defect that is higher than or equal to a predetermined threshold value overlaps with the region of interest. Further, the defect-region storage means may store the defect region that has been detected in a radiographic image obtained by performing radiography at an irradiation dose lower than the irradiation dose of a main radiography operation before the main radiography operation. Alternatively, the defect-region storage means may store the defect region that has been detected by calibration that is performed regularly.

Further, the movement amount calculation means may calculate a single movement direction and the movement amount for the single movement direction. Alternatively, the movement amount calculation means may calculate, as candidate movement amounts, a plurality of relative movement amounts for moving the radiographic image detector and/or the subject in different directions. At this time, the movement control means may select one of the candidate movement amounts, and control the operation for moving the radiographic image detector and/or the subject. Further, when the movement control means selects a candidate movement amount out of the plurality of candidate movement amounts, the movement control means may automatically select a candidate movement amount that has a smallest movement amount. Alternatively, the movement control means may select a candidate movement amount based on an instruction input by an operator (radiographer).

The radiographic image detection apparatus may further include an image correction means that corrects, based on the relative movement amount of the radiographic image detector and/or the subject, the radiographic image that has been obtained in a state in which the radiographic image detector and/or the subject has been moved by the relative-position changing means.

The radiographic image detection apparatus may further include a display control means that causes a display device to display a result of judgment by the overlap judgment means.

According to the radiographic image detection apparatus of the present invention and the method for controlling the apparatus, the apparatus includes:
a radiation source that outputs radiation to a subject;
a radiographic image detector that obtains a radiographic image by detecting the radiation that has been output from the radiation source to the subject and that has passed through the subject;
a relative-position changing means that moves at least one of the radiographic image detector and the subject to change the relative positions of the radiographic image detector and the subject with respect to each other; and
a defect-region storage means. Further, the method includes the steps of:
setting a region of interest in the radiographic image detector;
judging whether a defect region that has been stored in the defect-region storage means in advance is included in the set region of interest;
calculating a relative movement amount for changing the relative positions so that the defect region is not included in the region of interest when it has been judged that the defect region is included in the region of interest; and
moving, based on the calculated relative movement amount, the at least one of the radiographic image detector and the subject relative to each other by the relative-position changing means. Therefore, the at least one of the radiographic image detector and the subject is moved with respect to each other based on the relative positions of the region of interest, which is used for diagnosis using the image, and the defect region with respect to each other. Hence, unlike the conventional methods, it is not necessary to obtain radiographic images in the entire detection range on the radiographic image detector. Consequently, it is possible to prevent deterioration of the image quality of the radiographic image caused by the defect region while the dose of radiation that irradiates the subject is reduced.

Further, when the relative-position changing means moves at least one of the radiographic image detector and the subject in parallel or rotationally with respect to a detection surface of the radiographic image detector, the flexibility of the relative movement of the at least one of the radiographic image detector and the subject can be improved, and the relative movement amount of the at least one of the radiographic image detector and the subject can be reduced. Therefore, it is possible to efficiently move the radiographic image detector and/or the subject.

Further, when the defect-region storage means stores the size of the defect region and the degree of the defect of the defect region together with the position of the defect region, and the overlap judgment means judges whether the defect region having a size that is larger than or equal to a predetermined threshold value and the degree of the defect that is higher than or equal to a predetermined threshold value overlaps with the region of interest, at least one of the radiographic image detector and the subject is moved relative to each other only when a defect region that substantially affects (deteriorates) the image quality is present. Therefore, it is possible to prevent unnecessary relative movement of the radiographic image detector or the subject with respect to each other.

Further, when the movement amount calculation means calculates, as candidate movement amounts, a plurality of relative movement amounts for moving at least one of the radiographic image detector and the subject in different directions, and the movement control means selects one of the candidate movement amounts and controls the operation for moving the at least one of the radiographic image detector and the subject, the direction of the movement of the at least one of the radiographic image detector and the subject can be determined based on the environment in which the radiographic image detection apparatus is used. Specifically, the direction of the movement can be determined based on the environment, such as the size of a room in which the apparatus is set and the type or characteristic of the subject. Therefore, it is possible to improve the usability of the apparatus.

When the radiographic image detection apparatus further includes an image correction means that corrects, based on the relative movement amount of the at least one of the radiographic image detector and the subject, the radiographic image that has been obtained in a state in which the at least one of the radiographic image detector and the subject has been moved by the relative-position changing means, even if the position of the region of interest in the radiographic image is shifted by the parallel movement of the at least one of the radiographic image detector and the subject, or even if the subject in the radiographic image is inclined by the rotational movement, it is possible to prevent deterioration of the image quality by performing correction based on the relative movement amount.

When the radiographic image detection apparatus further includes a display control means that causes a display device to display a result of judgment by the overlap judgment means, the operator (radiographer) can recognize the relative positions of the region of interest and the defect region with respect to each other. Therefore, the operator can judge in advance (before actual radiography) whether at least one of the radiographic image detector and the subject needs to be moved relative to each other.

BRIEF DESCRIPTION OF THE DRAWINGS

FIG. 2 is a block diagram illustrating the radiographic image detection apparatus according to an embodiment of the present invention;

DESCRIPTION OF THE PREFERRED EMBODIMENTS

Figure 1:
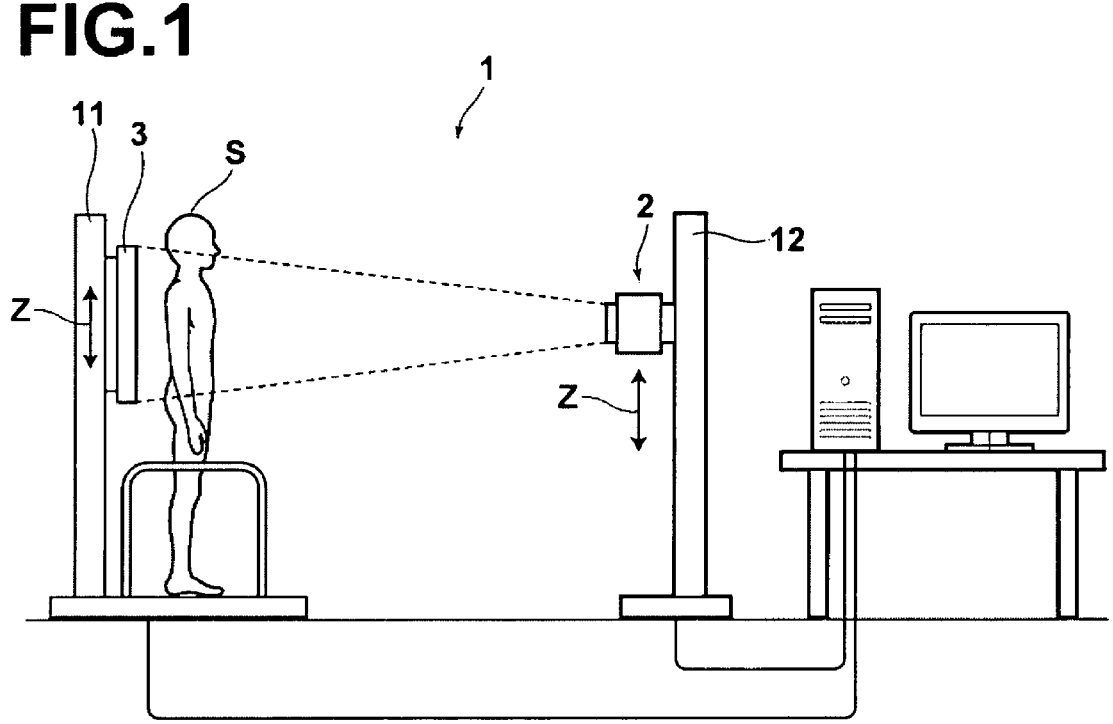
FIG. 1 is a schematic diagram illustrating a radiographic image detection apparatus according to an embodiment of the present invention.

Hereinafter, a radiographic image detection apparatus of the present invention will be described with reference to drawings. FIG. 1 is a schematic diagram illustrating an embodiment of a radiographic image detection apparatus for obtaining radiographic images. FIG. 2 is a block diagram of the radiographic image detection apparatus. A radiographic image detection apparatus 1 includes a radiation source 2, a radiographic image detector 3, a relative-position changing means 11, and a radiation source movement means 12. The radiation source 2 outputs radiation to subject S. The radiation source 2 is controlled by a movement control means 50. The radiographic image detector 3 stores, as a static latent image, radiographic image information represented by radiation that has passed through the subject S. Further, when the static latent image stored in the radiographic image detector 3 is read out, the distribution of transmittance of radiation (which has passed through the subject S) is detected as radiographic image P. The structure of the radiographic image detector 3 is not limited as long as radiation is detected and the detected radiation is output as image information. For example, the radiographic image detector 3 may be a TFT type solid-state detector. Alternatively, the radiographic image detector 3 may be a light-readout-type solid-state detector.

Figure 3A:
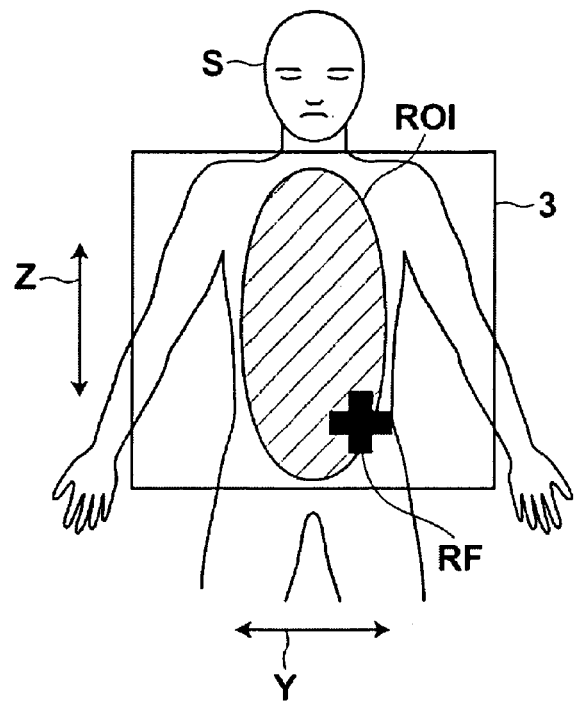
FIG. 3A is a diagram illustrating a state in which the radiographic image detector illustrated in FIG. 1 is positioned at a base position.
Figure 3B:
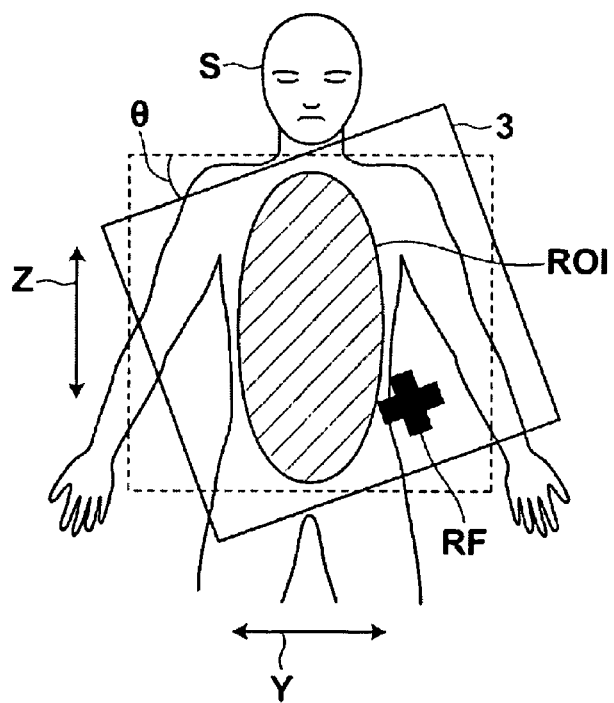
FIG. 3B is a diagram illustrating a state in which the radiographic image detector illustrated in FIG. 1 has been rotationally moved.
Figure 3C:
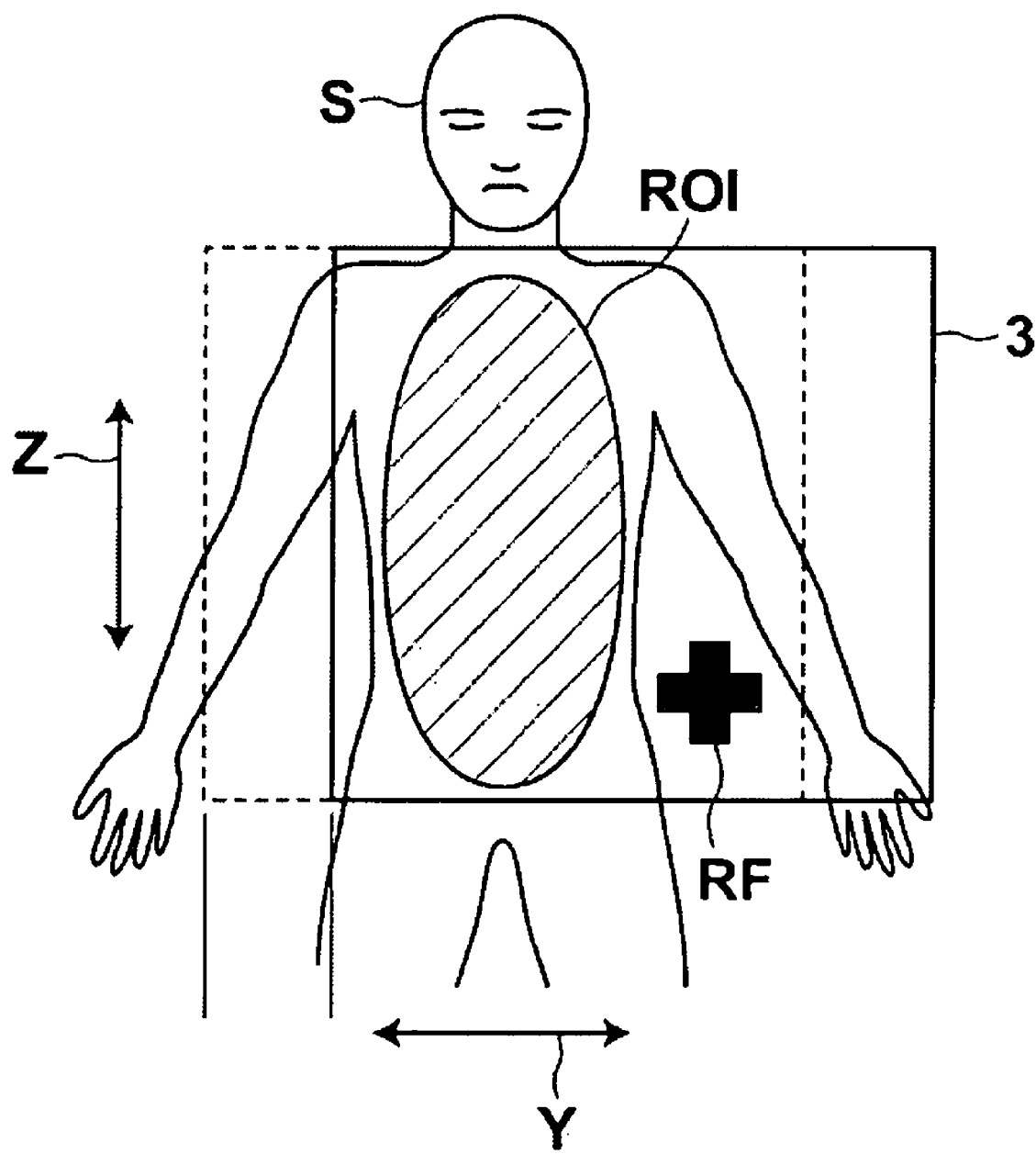
FIG. 3C is a diagram illustrating a state in which the radiographic image detector illustrated in FIG. 1 has been moved in parallel.

The relative-position changing means 11 moves the radiation detector 3 to change the relative positions of the radiographic image detector 3 and the subject S with respect to each other. Specifically, the relative-position movement means 11 may move the radiographic image detector 3 in parallel to a detection surface of the radiographic image detector 3 (in the direction of arrow Y and in the direction of arrow Z). Alternatively, the relative-position movement means 11 may rotationally move the radiographic image detector 3 with respect to the detection surface of the radiographic image detector. For example, the relative-position movement means 11 includes a rail, a bearing, and a drive means, such as a motor. FIGS. 3A through 3C are diagrams illustrating the states of moving the radiographic image detector 3. For example, the relative-position changing means 11 may rotationally move the radiographic image detector 3 positioned at a base position, as illustrated in FIG. 3A, by a rotation angle (direction) θ. The radiographic image detector 3 is positioned as illustrated in FIG. 3B after rotation. Alternatively, the relative-position changing means 11 may move the radiographic image detector 3 positioned at a base position, as illustrated in FIG. 3A, in a horizontal direction (the direction of arrow Y) or in a vertical direction (the direction of arrow Z). The radiographic image detector 3 is positioned as illustrated in FIG. 3C after movement in the horizontal direction or in the vertical direction.

The relative-position changing means 11 moves the radiographic image detector 3 based on control by the movement control means 50, and changes the relative positions of the radiographic image detector 3 and the subject S with respect to each other. It is not necessary that the radiographic image detector 3 is moved by a drive means. The radiographic image detector 3 may be structured in such a manner that an operator can manually change the relative position and the inclination of the radiographic image detector 3. In such a case, a handle may be attached to the radiographic image detector 3, and the relative-position changing means 11 may move the radiographic image detector 3 by application of force by an operator or power assist (a power assist means).

The radiation source movement means 12, illustrated in FIG. 1, moves the radiation source 2 to change the irradiation position of radiation based on the position of the radiographic image detector 3. In FIG. 1, the radiation source 2 is moved synchronously with the movement of the radiographic image detector 3. Alternatively, the irradiation position of radiation may be changed by swinging the radiation source 2.

In FIG. 2, the radiographic image detection apparatus 1 further includes a region-of-interest setting means 20, an overlap judgment means 30, a movement amount calculation means 40, and a movement control means 50. The region-of-interest setting means 20 sets a region at a predetermined position in the radiographic image detector 3 as a region of interest (ROI), as illustrated in FIGS. 3A through 3C. For example, the size, the shape and the base position of the region of interest (ROI) may be set in advance for each radiography mode and for each region to be radiographed. Further, the region-of-interest setting means 20 may automatically set the size, the shape and the base position of the region of interest (ROI) based on the radiography mode and the region to be radiographed that are input by an operator. Alternatively, the region-of-interest setting means 20 may set a region of interest (ROI) based on an input by the operator.

The overlap judgment means 30 judges whether the region of interest (ROI) set by the region-of-interest setting means 20 includes the defect region RF stored in the defect-region storage means FDB. Meanwhile, the defect-region storage means FDB stores the position of the defect region RF that cannot obtain correct image information together with the size of the defect region RF and the degree of deterioration of the image quality caused by the defect. Further, the defect-region storage means FDB may store the defect region RF that has been detected in a radiographic image obtained by performing radiography at an irradiation dose lower than the irradiation dose of a main radiography operation before the main radiography operation. Alternatively, the defect region RF may be updated by calibration that is performed regularly.

The overlap judgment means 30 judges whether the defect region RF is included in the region of interest (ROI) (please refer to FIG. 3A). Especially, the overlap judgment means 30 may make the judgment only with respect to the defect region (defect regions) RF of all of the defect regions stored in the defect-region storage means FDB that has a size and the degree of defect that substantially affect the deterioration of the image quality. The overlap judgment means 30 extracts the defect region RF having a size that is larger than or equal to a predetermined threshold value and the degree of the defect that is higher than or equal to a predetermined threshold value. Further, the overlap judgment means 30 judges whether the extracted defect region RF is included in the region of interest (ROI). Therefore, even if a defect region RF that does not affect the deterioration of the image is present in the region of interest, the radiographic image detector 3 is not moved. Hence, efficient radiography is possible. The aforementioned threshold value (values) may be set in advance. Alternatively, the threshold value (values) may be input by the operator.

The movement amount calculation means 40 calculates the relative positions of the subject S and the radiographic image detector 3 so that the defect region RF is not included in the region of interest (ROI) when the overlap judgment means 30 has judged that the defect region RF is included in the region of interest (ROI). The movement amount calculation means 40 has information about the possible movement range of the radiographic image detector 3, in which the radiographic image detector 3 can be moved by the relative-position changing means 11. The movement amount calculation means 40 calculates the relative movement amount of the radiographic image detector 3 within the possible movement range of the radiographic image detector 3. Especially, the movement amount calculation means 40 may have a function of calculating, as candidate movement amounts, a plurality of relative movement amounts that can change the relative positions of the subject S and the radiographic image detector 3 so that the defect region RF is not included in the region of interest (ROI).

Specifically, when the region of interest (ROI) and the defect region RF are overlapped with each other, as illustrated in FIG. 3A, the radiographic image detector 3 may be moved as illustrated in FIG. 3B or 3C. In FIG. 3B, the radiographic image detector 3 is rotated. In FIG. 3C, the radiographic image detector 3 is moved in parallel. At this time, the movement amount calculation means 40 has a function of calculating, as candidate movement amounts, two relative movement amounts for two different directions as described above.

The movement control means 50 controls the relative-position changing means 11 so that the radiographic image detector 3 is moved to a relative position calculated by the movement amount calculation means 40. Here, when a plurality of relative positions are calculated by the movement amount calculation means 40, as described above, and the calculated plurality of relative positions are presented to the operator, the movement control means 50 may control the moving operation of the relative-position changing means 11 based on a candidate movement amount that has been selected from the plurality of candidate movement amounts by the operator. The movement control means 50 may move the radiographic image detector 3 based on a candidate movement amount that has the smallest movement amount among the plurality of candidate movement amounts. Alternatively, a priority may be set for the rotational movement or the parallel movement, and the movement control means 50 may move the radiographic image detector 3 based on the set priority.

The image correction means 60 corrects, based on the relative movement amount of the radiographic image detector 3, the radiographic image P that has been obtained in a state in which the radiographic image detector 3 has been moved by the relative-position changing means 11. Specifically, when radiography is performed by rotating the radiographic image detector 3, as illustrated in FIG. 3B, the image of the subject in the region of interest (ROI) in the radiographic image inclines in an opposite direction to the rotation of the radiographic image detector 3. In such a case, the image correction means 60 performs correction to rotate the region of interest (ROI) in the direction of the rotation of the radiographic image. Further, when radiography is performed by moving the radiographic image detector 3 in parallel, as illustrated in FIG. 3C, the region of interest (ROI) in the radiographic image P is located off from the center of the radiographic image P. In such a case, the image correction means 60 moves the region of interest (ROI) so that the ROI is present around at the center of the radiographic image P. Alternatively, the image correction means 60 performs trimming processing so that the ROI is present around at the center of the radiographic image P. When the radiographic image P after rotation basically has a circular shape, it is not necessary to perform correction processing.

A display control means 70 controls a display device 100 to display various kinds of information. For example, the display control means 70 has a function of outputting a result of judgment about the overlapped region by the overlap judgment means 30, as illustrated in FIG. 3A, to the display device 100. Further, the display control means 70 may have a function of clearly indicating an image defect when a radiographic image P1 corrected by the image correction means 60 is displayed. The image defect is clearly indicated by superposing image defect information on the radiographic image P1.

As described above, the judgment is focused on the region of interest (ROI), and only the overlap of the defect region RF with the ROI is judged. Therefore, unlike the conventional method, it is not necessary to perform radiography a plurality of times. Hence, it is possible to reduce the radiation dose that irradiates the subject S and to prevent the deterioration of the image quality at the same time. Further, even if a defect region RF is generated, it is possible to obtain a normal radiographic image P by moving the radiographic image detector 3. Therefore, even if a defect is generated in a part of the radiographic image detector 3, it is not necessary to replace the whole radiographic image detector 3. Hence, the lifetime of the radiographic image detector becomes longer, and the downtime of the apparatus becomes shorter.

Figure 4:
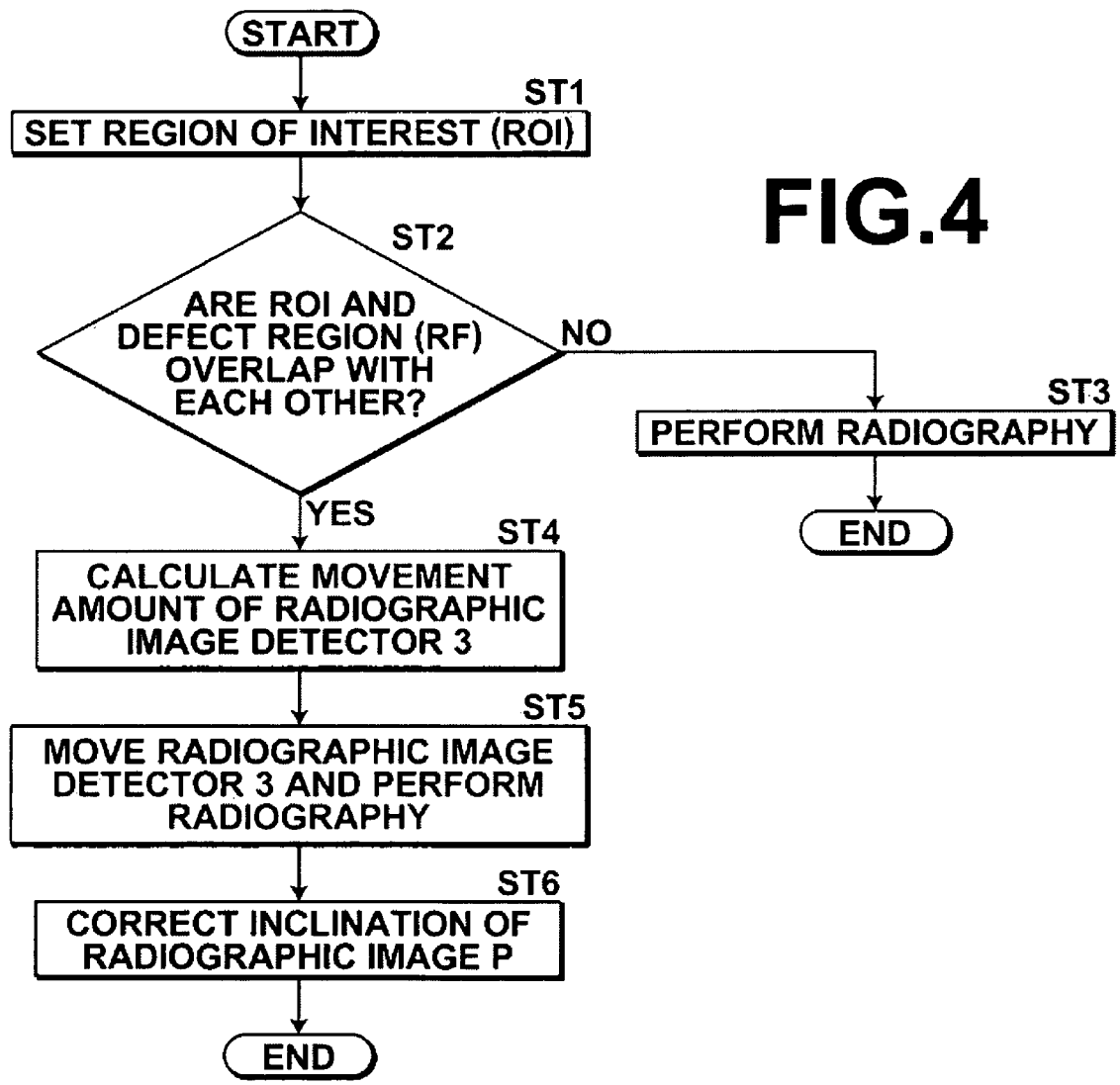
FIG. 4 is a flow chart illustrating an embodiment of a method for controlling the radiographic image detection apparatus according to the present invention.

FIG. 4 is a flow chart illustrating an embodiment of a method for controlling the radiographic image detection apparatus of the present invention. With reference to FIGS. 1 through 4, the method for controlling the radiographic image detection apparatus will be described. First, with a subject S standing in front of the radiographic image detector 3, the region-of-interest setting means 20 sets a region of interest (ROI) (step ST1). Then, the overlap judgment means 30 judges whether a defect region RF is present in the region of interest (ROI) (step ST2). When a defect region RF is not present in the region of interest (ROI), radiography is performed without moving the radiographic image detector 3 (step ST3).

In contrast, when a defect region RF is present in the region of interest (ROI) (please refer to FIG. 3A), the movement amount calculation means 40 calculates the relative movement amount of the radiographic image detector 3 with respect to the subject S (step ST4). Further, the relative-position changing means 11 operates by control by the movement control means 50. After the radiographic image detector 3 is moved by the calculated relative movement amount (please refer to FIGS. 3B and 3C), radiography is performed to detect a radiographic image P (step ST5). Then, the image correction means 60 performs correction processing on the radiographic image P detected by the radiographic image detector 3. The image correction means 60 corrects the inclination of the radiographic image P by the relative movement amount of the radiographic image detector 3, trims the radiographic image P, or the like (step ST6).

According to the aforementioned embodiments, the radiographic image detection apparatus includes the radiation source 2 that outputs radiation to the subject S, the radiographic image detector 3 that obtains a radiographic image by detecting the radiation that has been output from the radiation source 2 to the subject and that has passed through the subject S, the relative-position changing means 11 that moves the radiographic image detector 3 to change the relative positions of the radiographic image detector and the subject with respect to each other. Further, a region of interest (ROI) is set in the radiographic image detector 3, and judgment is made as to whether a defect region that has been stored in the defect-region storage means FDB in advance is included in the set region of interest. When it has been judged that the defect region is included in the region of interest ROI, a relative movement amount of the radiographic image detector 3 for changing the relative positions so that the defect region RF is not included in the region of interest (ROI) is calculated. Further, the radiographic image detector 3 is moved based on the calculated relative movement amount. Accordingly, the radiographic image detector 3 is moved based on the relative positions of the region of interest ROI, which is used for diagnosis using images, and the defect region RF. Therefore, unlike the conventional method, it is not necessary to obtain radiographic images for the entire detection range of the radiographic image detector 3. Hence, it is possible to reduce the radiation dose that irradiates the subject and to prevent deterioration of the image quality caused by the defect region at the same time.

Further, when the relative-position changing means 11 moves the radiographic image detector 3 in parallel or rotationally to the detection surface of the radiographic image detector 3, as illustrated in FIGS. 3A through 3C, it is possible to increase the flexibility of the movement of the radiographic image detector 3, and to reduce the relative movement amount of the radiographic image detector 3. Hence, it is possible to efficiently move the radiographic image detector 3.

Further, when the defect-region storage means FDB, illustrated in FIG. 2 stores the size of the defect (defect region RF) and the degree of the defect together with the position of the defect region RF, and when the overlap judgment means 30 judges whether the defect (defect region RF) having a size that is larger than or equal to a predetermined threshold value and the degree of the defect that is higher than or equal to a predetermined threshold value overlaps with the region of interest ROI, the radiographic image detector 3 is moved only when a defect region RF that substantially affects the deterioration of the image quality of the radiographic image is present. Therefore, it is possible to prevent unnecessary movement of the radiographic image detector 3.

Further, when the movement amount calculation means 40 calculates, as candidate movement amounts, a plurality of relative movement amounts for moving the radiographic image detector 3 in different directions, and the movement control means 50 selects one of the candidate movement amounts and controls the operation for moving the radiographic image detector 3 using the selected candidate movement amount, it is possible to determine the direction of the movement of the radiographic image detector 3 based on the environment, such as the size of a room in which the radiographic image detection apparatus is set and the type or characteristic of the subject. Therefore, it is possible to improve the usability of the apparatus.

When the radiographic image detection apparatus further includes the image correction means 60 that corrects, based on the relative movement amount of the radiographic image detector 3, the radiographic image that has been obtained in a state in which the radiographic image detector 3 has been moved by the relative-position changing means 11, even if the position of the region of interest in the radiographic image is shifted by the parallel movement of the radiographic image detector 3, or the subject in the radiographic image detector is inclined by the rotational movement of the radiographic image, it is possible to prevent the deterioration of the image quality by performing correction based on the relative movement amount.

When the radiographic image detection apparatus further includes the display control means that causes a display device to display a result of judgment by the overlap judgment means 30, the operator can recognize the relative positions of the region of interest (ROI) and the defect region RF with respect to each other. Therefore, the operator can judge whether the radiographic image detector 3 needs to be moved before performing actual radiography.

The embodiments of the present invention are not limited to the aforementioned embodiments. For example, when the size of an image defect (defect region) is large, or when a plurality of image defects (defect regions) are present, there are cases in which it is impossible to prevent overlapping between the region of interest (ROI) and the defect region RF. There are also cases in which a part of the region of interest (ROI) is positioned outside the detection range of the radiographic image detector. In such cases, the operator (radiographer) may set the region of interest (ROI) again by reducing the area of the ROI so that only an essential region to be focused is included. Alternatively, a restriction condition, such as the order of priority, may be used to set the region of interest (ROI). Further, a restriction condition, such as the number or the area of image defects (defect regions) that cannot avoid overlap, may be set.

Further, in FIG. 1, a standing-position-type radiographic image detection apparatus is illustrated as an example. The present invention is also applicable to a decubitus-type radiographic image detection apparatus, a mammographic apparatus, a radiation CT (computed tomography) apparatus, and the like. FIG. 1 illustrates a case in which the relative-position changing means 11 functions as a detector moving means for changing the relative positions of the radiographic image detector 3 and the subject S with respect to each other by moving the radiographic image detector 3. Alternatively, the subject S may be moved to change the relative positions of the radiographic image detector 3 and the subject S. Specifically, when a decubitus-type radiographic image detector apparatus is used, the relative-position changing means 11 may function as a subject moving means for changing the relative positions of the radiographic image detector 3 and the subject S with respect to each other by moving a bed on which the subject lies with respect to the radiographic image detector. Further, the relative-position changing means 11 may move both of the radiographic image detector 3 and the subject S with respect to each other to minimize the movement amount of each of the radiographic image detector 3 and the subject S.

What is claimed is:

1. A radiographic image detection apparatus comprising:
   a radiation source that outputs radiation to a subject;
   a radiographic image detector that obtains a radiographic image by detecting the radiation that has been output from the radiation source to the subject and that has passed through the subject;
   a relative-position changing means that moves at least one of the radiographic image detector and the subject to change the relative positions of the radiographic image detector and the subject with respect to each other;
   a defect-region storage means that stores the position of a defect region of the radiographic image detector;
   a region-of-interest setting means that sets a region of interest in the radiographic image detector;
   an overlap judgment means that judges whether the defect region stored in the defect-region storage means is included in the region of interest that has been set by the region-of-interest setting means;
   a movement amount calculation means that calculates a relative movement amount for changing the relative positions so that the defect region is not included in the region of interest when the overlap judgment means has judged that the defect region is included in the region of interest; and
   a movement control means that controls, based on the relative movement amount that has been calculated by the movement amount calculation means, an operation of the relative-position changing means for moving the at least one of the radiographic image detector and the subject.

2. A radiographic image detection apparatus, as defined in claim 1, wherein the relative-position changing means moves the at least one of the radiographic image detector and the subject in parallel or rotationally with respect to a detection surface of the radiographic image detector.

3. A radiographic image detection apparatus, as defined in claim 1, wherein the defect-region storage means stores the size of the defect region and the degree of the defect of the defect region together with the position of the defect region, and wherein the overlap judgment means judges whether the defect region having a size that is larger than or equal to a predetermined threshold value and the degree of the defect that is higher than or equal to a predetermined threshold value overlaps with the region of interest.

4. A radiographic image detection apparatus, as defined in claim 1, wherein the movement amount calculation means calculates, as candidate movement amounts, a plurality of relative movement amounts for moving the at least one of the radiographic image detector and the subject in different directions, and wherein the movement control means selects one of the candidate movement amounts and controls the operation for moving the at least one of the radiographic image detector and the subject.

5. A radiographic image detection apparatus, as defined in claim 1, further comprising:
   an image correction means that corrects, based on the relative movement amount of the at least one of the radiographic image detector and the subject, the radiographic image that has been obtained in a state in which the at least one of the radiographic image detector and the subject has been moved by the relative-position changing means.

6. A radiographic image detection apparatus, as defined in claim 1, further comprising:
   a display control means that causes a display device to display a result of judgment by the overlap judgment means.

7. A radiographic image detection apparatus, as defined in claim 1, wherein the defect-region storage means stores the defect region that has been detected in a radiographic image obtained by performing radiography at an irradiation dose lower than the irradiation dose of a main radiography operation before the main radiography operation.

8. A method for controlling a radiographic image detection apparatus that includes:
   a radiation source that outputs radiation to a subject;
   a radiographic image detector that obtains a radiographic image by detecting the radiation that has been output from the radiation source to the subject and that has passed through the subject;
   a relative-position changing means that moves at least one of the radiographic image detector and the subject to change the relative positions of the radiographic image detector and the subject with respect to each other; and
   a defect-region storage means, the method comprising the steps of:
   setting a region of interest in the radiographic image detector;
   judging whether a defect region that has been stored in the defect-region storage means in advance is included in the set region of interest;
   calculating a relative movement amount for changing the relative positions so that the defect region is not included in the region of interest when it has been judged that the defect region is included in the region of interest; and
   moving, based on the calculated relative movement amount, the at least one of the radiographic image detector and the subject relative to each other by the relative-position changing means.

* * * * *